US006193656B1

(12) United States Patent
Jeffries et al.

(10) Patent No.: US 6,193,656 B1
(45) Date of Patent: Feb. 27, 2001

(54) INTRAOCULAR PRESSURE MONITORING/ MEASURING APPARATUS AND METHOD

(76) Inventors: Robert E. Jeffries, 1603 S. 15th Pl., Rogers, AR (US) 72758; Lee Birchansky, 2635 Granite Ct. NE., Cedar Rapids, IA (US) 52402

(*) Notice: Subject to any disclaimer, the term of this patent is extended or adjusted under 35 U.S.C. 154(b) by 0 days.

(21) Appl. No.: 09/246,379

(22) Filed: Feb. 8, 1999

(51) Int. Cl.⁷ .................................. A61B 5/00; A61B 3/16
(52) U.S. Cl. ................................. 600/398; 600/561
(58) Field of Search .................... 600/383, 398, 600/399, 400, 402, 547, 552, 561; 623/4, 6, 4.1, 6.11

(56) References Cited

U.S. PATENT DOCUMENTS

| | | | |
|---|---|---|---|
| 3,597,964 | 8/1971 | Herrsching et al. | 73/80 |
| 3,763,696 | 10/1973 | Krakau | 73/80 |
| 3,977,237 | 8/1976 | Tesi | 73/80 |
| 4,089,329 | * 5/1978 | Couvillon, Jr. et al. | 128/2 T |
| 4,127,110 | 11/1978 | Bullara | 128/2 P |
| 4,305,399 | * 12/1981 | Beale | 128/645 |
| 4,705,045 | 11/1987 | Nishimura | 128/648 |
| 4,759,370 | 7/1988 | Kozin et al. | 128/645 |
| 4,816,031 | 3/1989 | Pfoff | 623/6 |
| 4,860,755 | 8/1989 | Erath | 128/645 |
| 4,886,066 | 12/1989 | Ingalz et al. | 128/645 |
| 4,922,913 | * 5/1990 | Waters, Jr. et al. | 128/645 |
| 4,928,697 | 5/1990 | Hsu | 128/645 |
| 4,978,354 | * 12/1990 | Van Gent | 623/6 |
| 5,002,056 | 3/1991 | Takahashi et al. | 128/648 |
| 5,005,577 | 4/1991 | Frenkel | 128/645 |
| 5,033,841 | 7/1991 | Nishio et al. | 351/212 |
| 5,109,852 | * 5/1992 | Kaye et al. | 128/645 |
| 5,131,739 | 7/1992 | Katsuragi | 351/212 |
| 5,148,807 | 9/1992 | Hsu | 128/645 |
| 5,165,409 | 11/1992 | Coan | 128/652 |
| 5,176,139 | 1/1993 | Federov et al. | 128/645 |
| 5,190,042 | 3/1993 | Hock | 128/652 |
| 5,197,473 | 3/1993 | Fedorov et al. | 128/645 |
| 5,299,573 | 4/1994 | Kobayashi | 128/645 |
| 5,337,747 | * 8/1994 | Neftel | 128/635 |
| 5,349,955 | 9/1994 | Suzuki | 128/645 |

(List continued on next page.)

FOREIGN PATENT DOCUMENTS

99/01063    1/1999   (WO) ............................ A61B/3/16

OTHER PUBLICATIONS

Kalvesten, E., et al., "The First Surface Micromachined Pressure Sensor for Cardiovascular Pressure Measurements", 574–579.

Burns, D. et al., "Sealed–cavity resonant microbeam pressure sensor", *Sensors and Actuators A*, 48:179–186 (1995).

Zook, J. et al., "Optically excited self–resonant microbeams", *Sensors and Actuators A*, 52:92–98 (1996).

Puers, R., "Capacitive sensors: when and how to use them", *Sensors and Actuators, A.CH,* Elsevier Sequoia S.A., vol. A37/38, XP000411381, 93–105, (Jun. 1, 1993).

Rosengren, L., et al., "A System for Passive Implantable Pressure Sensors", *Sensors and Actuators A.CH.* Elsevier Sequoia S.A., vol. A43, No. 1/03, XP000454087, 55–58, (May 1, 1994).

Van Schuylenbergh, K., et al., "Passive Telemetry by Harmonics Detection", Ann. Int'l Conf of the IEEE Engineering in Medicine and Biology Society, XP000787643, 299–300, (1997).

*Primary Examiner*—Cary O'Connor
*Assistant Examiner*—Charles Marmor, II
(74) *Attorney, Agent, or Firm*—Schwegman, Lundberg, Woessner & Kluth, P.A.

(57) ABSTRACT

An apparatus and method of monitoring/measuring intraocular pressure in an eye includes a miniature pressure sensor having an attachment for connecting the miniature pressure sensor to the iris of the eye or an intraocular lens. The miniature pressure sensor is preferably a Polysilicon Resonant Transducer (PRT).

24 Claims, 5 Drawing Sheets

U.S. PATENT DOCUMENTS

| | | | |
|---|---|---|---|
| 5,355,884 | 10/1994 | Bennett | 128/645 |
| 5,375,595 | 12/1994 | Sinha et al. | 128/645 |
| 5,433,701 * | 7/1995 | Rubinstein | 604/8 |
| 5,474,066 | 12/1995 | Grolman | 128/645 |
| 5,480,426 * | 1/1996 | Chu | 623/6 |
| 5,523,808 | 6/1996 | Kohayakawa | 351/210 |
| 5,546,941 | 8/1996 | Zeimer et al. | 128/652 |
| 5,559,358 | 9/1996 | Burns et al. | 257/431 |
| 5,634,463 | 6/1997 | Hayafuji | 128/645 |
| 5,671,737 | 9/1997 | Harosi | 128/645 |
| 5,727,551 | 3/1998 | Takagi | 128/648 |
| 5,836,873 | 11/1998 | Fresco | 600/398 |
| 5,840,041 * | 11/1998 | Petter et al. | 600/547 |
| 5,964,704 | 10/1999 | Hayafuji | 600/401 |
| 6,030,343 | 2/2000 | Chechersky et al. | 600/399 |

* cited by examiner

INTRAOCULAR PRESSURE MONITORING/MEASURING APPARATUS AND METHOD

FIELD OF THE INVENTION

The present invention relates to an intraocular pressure measuring/monitoring apparatus and method thereof, and more particularly to an in situ intraocular pressure monitoring/measuring apparatus and method thereof.

BACKGROUND OF THE INVENTION

The American Academy of Ophthalmology has reported that about two million people in the United States have primary open angle glaucoma (the most common of several types of glaucoma). About seven million office visits are made each year by people with glaucoma or those suspected of having glaucoma. Glaucoma is the second leading cause of legal blindness in the United States and the leading cause of legal blindness in African-Americans. About 80,000 people in the United States alone are legally blind from glaucoma, not counting those with lesser visual impairment.

By definition, glaucoma is a group of eye diseases characterized by an increase in intraocular pressure which causes pathological changes in the optic disc and nerve fiber layer of the retina with resultant typical defects in the field of vision. The relationship between glaucoma and intraocular pressure is fundamental to proper treatment planning for glaucoma.

Normal intraocular pressure is considered to be less than 22 mm Hg. However, at least one in six patients with glaucoma may have pressure below this normal level and yet still have progressive eye damage. Also, at any single test, about one half of all glaucoma patients will exhibit measured intraocular pressures below 22 mm Hg but actually will have average intraocular pressures higher than 22 mm Hg. This makes frequent testing necessary to obtain an accurate assessment of a patient's average intraocular pressure.

Most current methods of routine intraocular pressure measurements rely on applanating a plunger against the cornea. The degree to which a portion of the cornea is deformed indicates the pressure inside the eye resisting this deformation. All of these methods are inferring the intraocular pressure rather than measuring it directly. Some specialists believe that the thickness of the cornea can vary from person to person, and that other factors such as corneal scars or previous surgery may affect the accuracy of these measurements. Also, most of these methods require that topical anesthesia be placed on the cornea prior to measuring the pressure and the measurements be made by trained personnel. Therefore, there is a need to develop techniques to make repeated and/or continuous measurements and to enable persons other than trained personnel to make such measurements.

U.S. Pat. No. 5,005,577 discloses an intraocular lens pressure monitoring device based on radiosonde technology. Radiosonde technology has been around for decades. The idea of using radiosonde technology for intraocular pressure monitoring was proposed in the '577 patent. However, it is unknown from the '577 patent how to make or use such an intraocular pressure monitoring device to carry out the invention. Specifically, the technology disclosed in the '577 patent has not been miniaturized in such a way to make it possible to insert into the eye.

Further, the '577 patent discloses an intraocular lens pressure monitoring device as a part of an integrated intraocular lens system, not a stand-alone device. If replacement of the monitoring device is needed, it would be difficult to separate the device from the lens without major surgery.

The '577 patent also discloses active sensors. An active sensor usually includes a power supply and a transmitter. As indicated in the '577 patent, an active sensor is generally too large in size to be implanted in the eye. Although it is speculated that technology will progress to the point to allow an active sensor to be implanted in the eye, the patentee does not, in fact, know what technology may be used and how it could be used to resolve the above-mentioned problems and addresses the above-mentioned concerns.

Accordingly, there is a need for a miniaturized device capable of inserting into an eye to monitor/measure intraocular pressure accurately, frequently, and continuously. There is also a need for a stand-alone intraocular pressure monitoring/measuring device separate from an intraocular lens system.

SUMMARY OF THE INVENTION

The present invention relates to an intraocular pressure measuring/monitoring apparatus and method thereof, and more particularly to an in situ intraocular pressure monitoring/measuring apparatus and method thereof.

The present invention discloses a miniature apparatus capable of monitoring intraocular pressure in an eye. The apparatus includes a miniature pressure sensor having an attachment for connecting the sensor to a site in the eye. For example, the sensor can be attached to the front surface of the periphery of the iris, accomplished by suturing, clamping, and the like, or incorporated into an intraocular lens for implantation at the time of cataract surgery.

In one aspect of the present invention, the pressure sensor is a Polysilicon Resonant Transducer (PRT) or a similarly suitable transducer. PRT technology allows accurate intraocular pressure measurements. Further, the apparatus using PRT technology is small enough to allow implantation into the eye without impeding eye function. In the present invention, the PRT can be encased in materials such as silicone, acrylic polymer, polymethylmethacrylate (PMMA), and the like. These materials have been used to make intraocular lenses and are proven safe for implantation into the eye.

In one embodiment of the present invention, the PRT is a fully self-contained, stand-alone device. The PRT is operated by irradiating it with laser light. The PRT resonates to this light in such a way that is indicative of the pressure of the environment in which it resides. The resonance of the reflected laser light is proportional to the ambient pressure surrounding the device, e.g. within the eye. Alternatively, if the PRT is placed behind the iris, e.g. proximate to an intraocular lens, or as a part of an intraocular lens implant, non-visible wavelengths of light can be used. These frequencies of light will penetrate the tissue of the iris and interact with the device to monitor/measure the intraocular pressure.

In another aspect of the present invention, the PRT apparatus can be placed in the eye as an outpatient procedure, as an office procedure, or as a part of a cataract surgery. This technique will provide direct intraocular pressure measurements.

An advantage of the present invention is that the pressure measurements can be taken at any time without the need for a topical anesthesia or a trained person. The measurements can be taken by the patients themselves at home. A further advantage is that the present invention allows continuous measurements throughout the day or night, and even through a closed eyelid. This would allow therapy to be tailored to the patient's needs. Moreover, the effect and timing of glaucoma medications can be monitored much more efficiently than through the use of traditional techniques.

BRIEF DESCRIPTION OF THE DRAWINGS

A better understanding of the construction and operational characteristics of a preferred embodiment(s) can be realized from a reading of the following detailed description, especially in light of the accompanying drawings in which like reference numerals in the several views generally refer to corresponding parts.

DETAILED DESCRIPTION OF THE PREFERRED EMBODIMENTS

The miniature apparatus of the present invention is capable of monitoring intraocular pressure in an eye. The apparatus includes a miniature pressure sensor having an attachment for connecting the sensor to a site in the eye. The apparatus may be a passive (i.e. no power source), miniature electronic circuit such as an integrated circuit chip with a sensor component for interaction with optic, electromagnetic, sonic, or other energy forms. The circuit also includes a pressure detecting component that changes circuit response as a function of pressure.

In the following description of the exemplary embodiment, reference is made to the accompanying drawings which form a part hereof, and in which is shown by way of illustration the specific embodiment in which the invention may be practiced. It is to be understood that other embodiments may be made without departing from the scope of the present invention.

Figure 1:
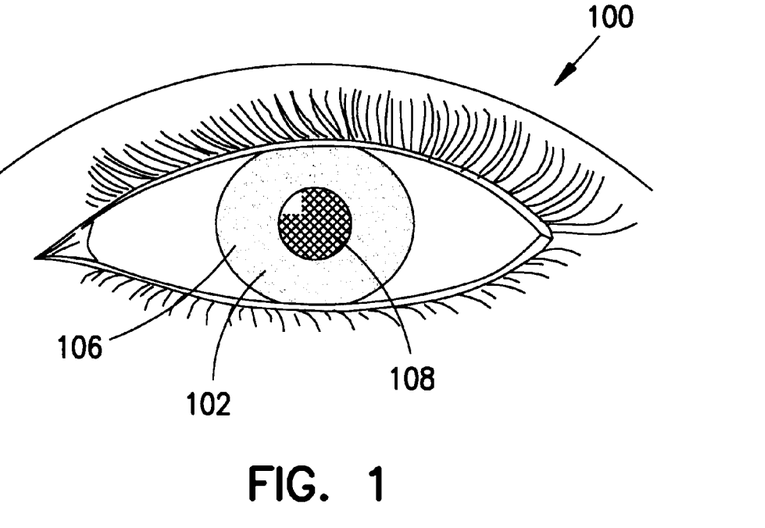
FIG. 1 is a front outside view of an eye for which an intraocular pressure monitoring/measuring apparatus in accordance with the present invention can be adapted.
Figure 2:
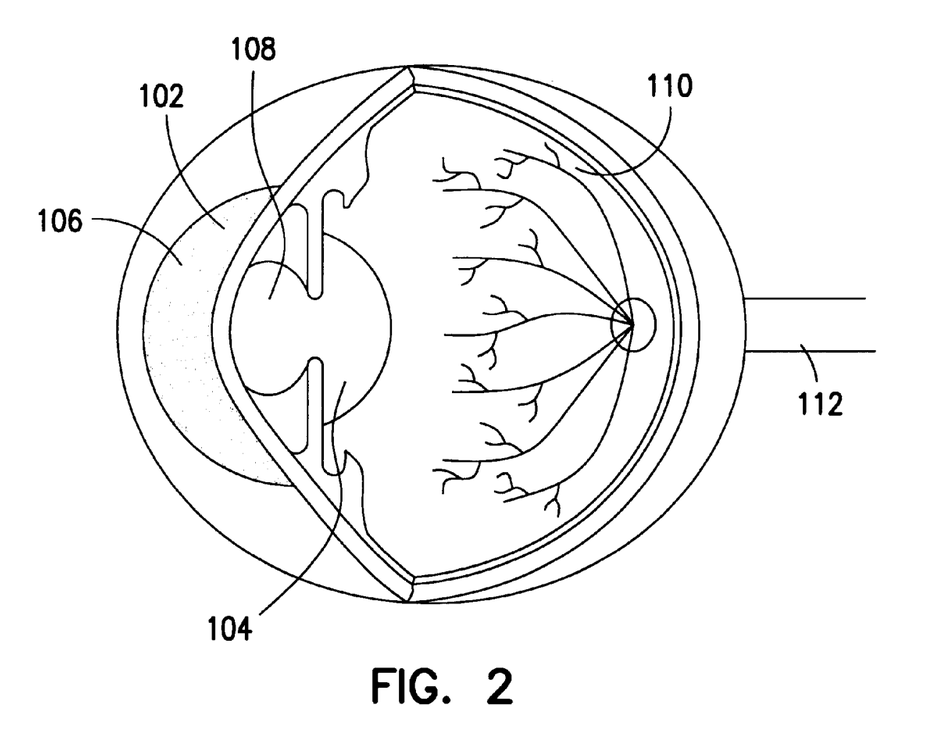
FIG. 2 is a cross-sectional inside view of the eye for which the intraocular pressure monitoring/measuring apparatus can be adapted.

Referring now to FIGS. 1 and 2, there is generally illustrated major components of an eye 100 including an iris 102, a natural crystalline lens 104, a cornea 106, a pupil 108, a retina 110, and an optic nerve 112. An intraocular pressure monitoring/measuring apparatus adapted in the eye will be discussed below.

Figure 3:
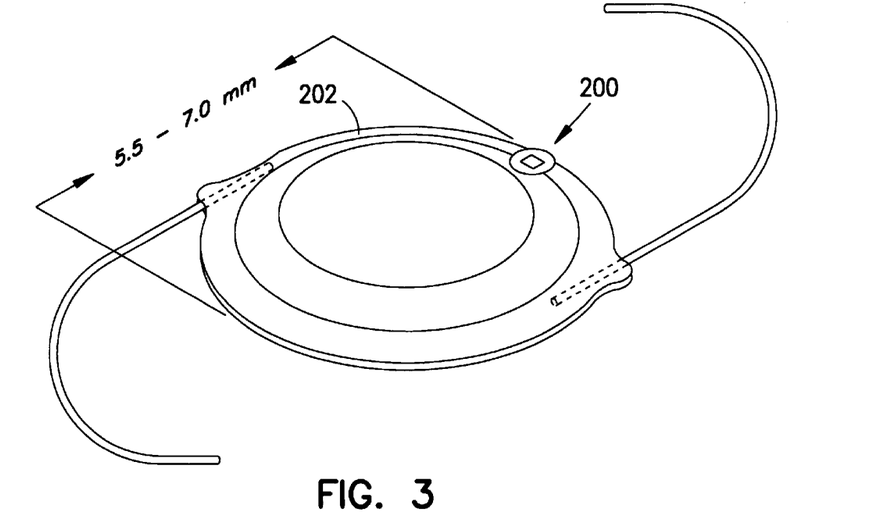
FIG. 3 is an enlarged perspective view of an intraocular pressure monitoring/measuring apparatus incorporated into an intraocular lens.

FIG. 3 is an enlarged perspective view of an intraocular pressure monitoring/measuring apparatus or pressure sensor 200 incorporated into an intraocular lens 202, such as a typical polymethylmethacrylate (PMMA) intraocular lens. The intraocular lens 202 may be inserted into the eye in place of the natural crystalline lens 104 in FIG. 1 at the time of a cataract surgery. Similar intraocular lenses can be made of silicone, acrylic or PMMA, etc. The intraocular pressure monitoring/measuring apparatus 200 can be a polysilicon resonant transducer (PRT). For illustrative purposes, the PRT 200 is shown in FIGS. 3–11. The PRT 200 may be incorporated into the edge of the lens 202 itself (FIG. 3) or onto one of arms (haptics) 204 used for fixating the lens 202 in the center of the eye after implantation into the eye. The majority of intraocular lenses 202 are implanted behind the iris 102 where the natural crystalline lens 104 once resided. However, the intraocular lens 202 may also be implanted in front of the iris 102 in selected patients.

It is appreciated that if desired, the PRT 200 can be incorporated into an eye with the natural crystalline lens 104 in place within the scope of the present invention. It is also appreciated that for illustrative purposes, the PRT 200 and the intraocular lens 202 are not shown in a normal scale. In a preferred embodiment, the intraocular lens 202 may have a diameter of 5.5–7.0 mm, and the PRT 200 may have one millimeter square or less. It is appreciated that other suitable sizes may be used without departing from the principles of the present invention.

Figure 4:
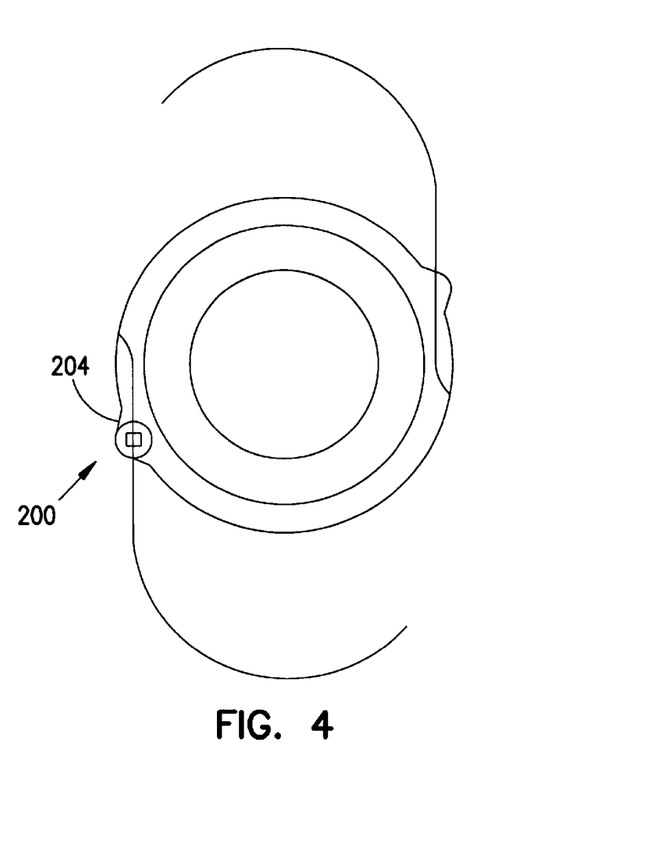
FIG. 4 is an enlarged elevational view of the intraocular pressure monitoring/measuring apparatus incorporated on a lens' haptic.
Figure 5:
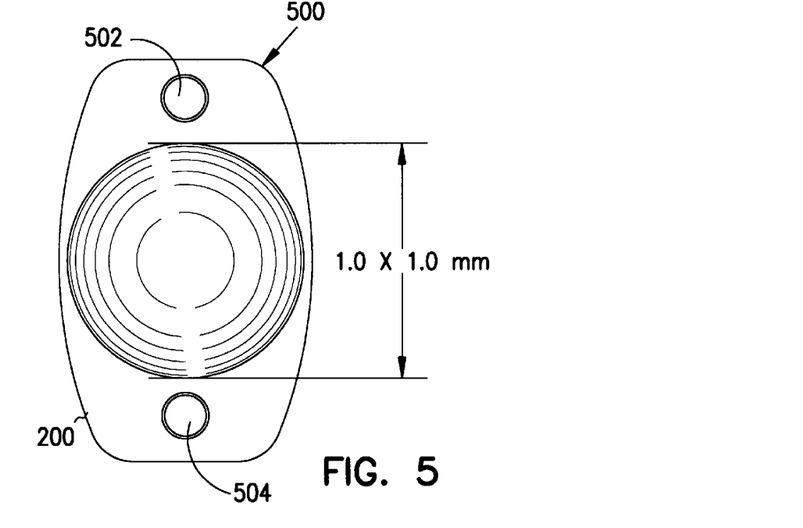
FIG. 5 is an enlarged front elevational view of the intraocular pressure monitoring/measuring apparatus to be attached to an iris of the eye.
Figure 6:
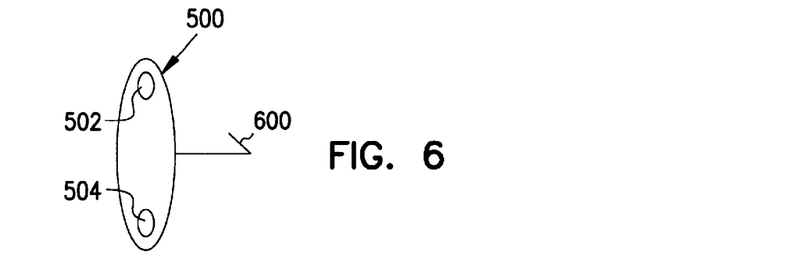
FIG. 6 is an enlarged side elevational view of the intraocular pressure monitoring/measuring apparatus with a barb for attaching the apparatus to the iris of the eye.
Figure 7:
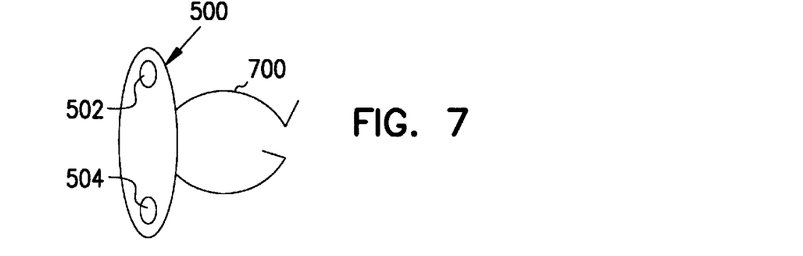
FIG. 7 is an enlarged side elevational view of the intraocular pressure monitoring/measuring apparatus with a locking clamp for attaching the apparatus to the iris of the eye.
Figure 8:
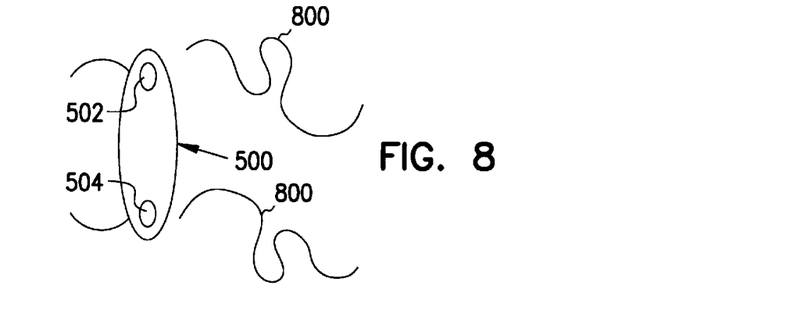
FIG. 8 is an enlarged side elevational view of the intraocular pressure monitoring/measuring apparatus with suturing strings for attaching the apparatus to the iris of the eye.

FIGS. 5–8 illustrate various exemplary techniques of attaching the PRT 200 onto an internal tissue, e.g. the iris 102. The PRT 200 may be constructed to be enclosed in a housing 500 with eyelets 502, 504 for suturing. The PRT 200 is disposed at a central region of the housing 500. As mentioned above, the PRT 200 is preferably in a dimension of 1 mm by 1 mm or less. The housing 500 may be made of silicone, acrylic or polymethylmethacrylate (PMMA) materials. The housing 500 may be incorporated into the intraocular lens 202 as shown in FIGS. 3 or 4. Alternatively, the housing 500 may be attached to the iris 102 by passing suture materials 800 through the eyelets 502, 504 of the housing 500 as shown in FIG. 8.

Another attachment technique is shown in FIG. 6. A small barb 600 resembling a fishing hook made of prolene (an inert suturing material) or a similar inert material may be attached to the PRT housing 500. The barb 600 may be used to impale the iris 102 allowing attachment of the PRT 200 onto the front surface of the iris 102.

A further attachment technique is shown in FIG. 7. A clamping device 700 of similar material may also be used to crimp the PRT 200 around a small portion of the iris tissue allowing attachment of the PRT 200 to the iris 102.

Figure 9:
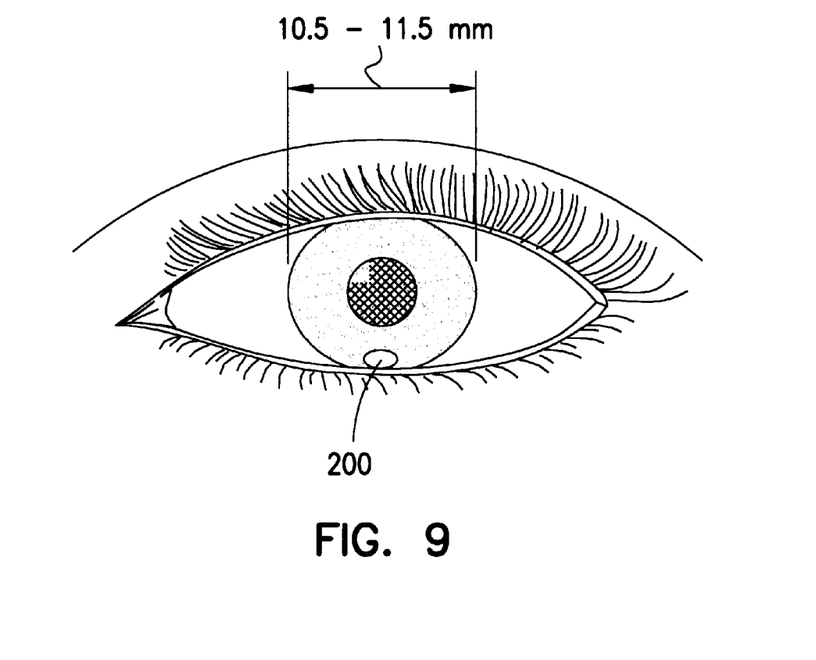
FIG. 9 is a front outside view of the eye with the intraocular pressure monitoring/measuring apparatus attached on the iris.
Figure 10:
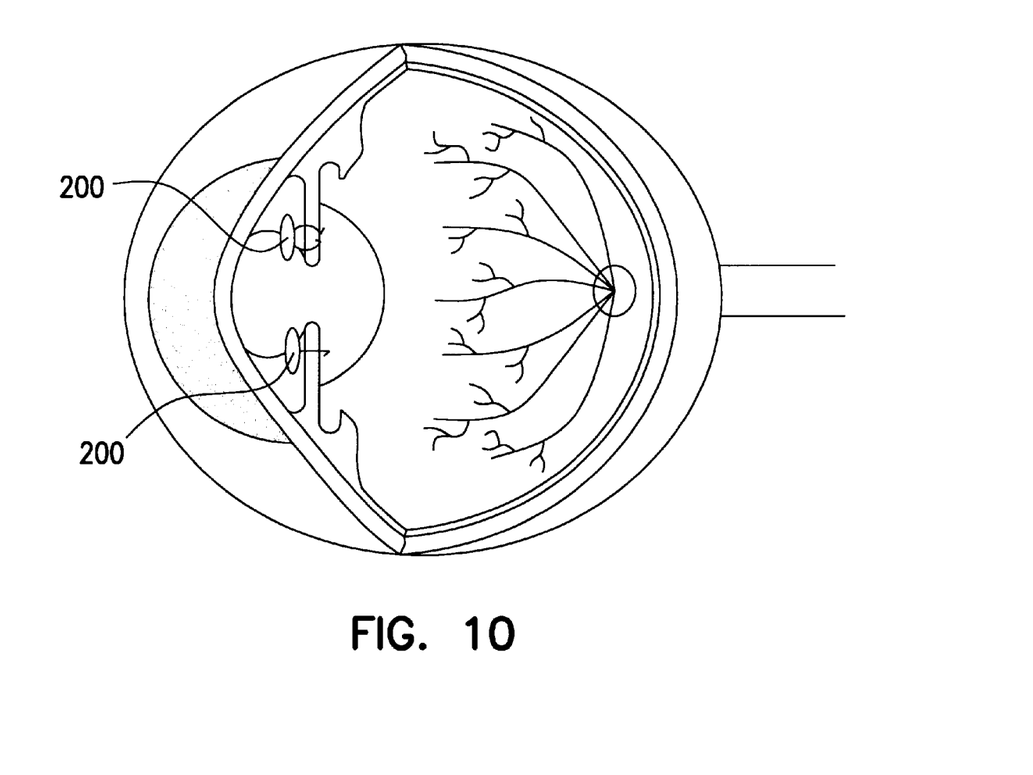
FIG. 10 is a cross-sectional inside view of the eye with the intraocular pressure monitoring/measuring apparatus attached on the iris.
Figure 11:
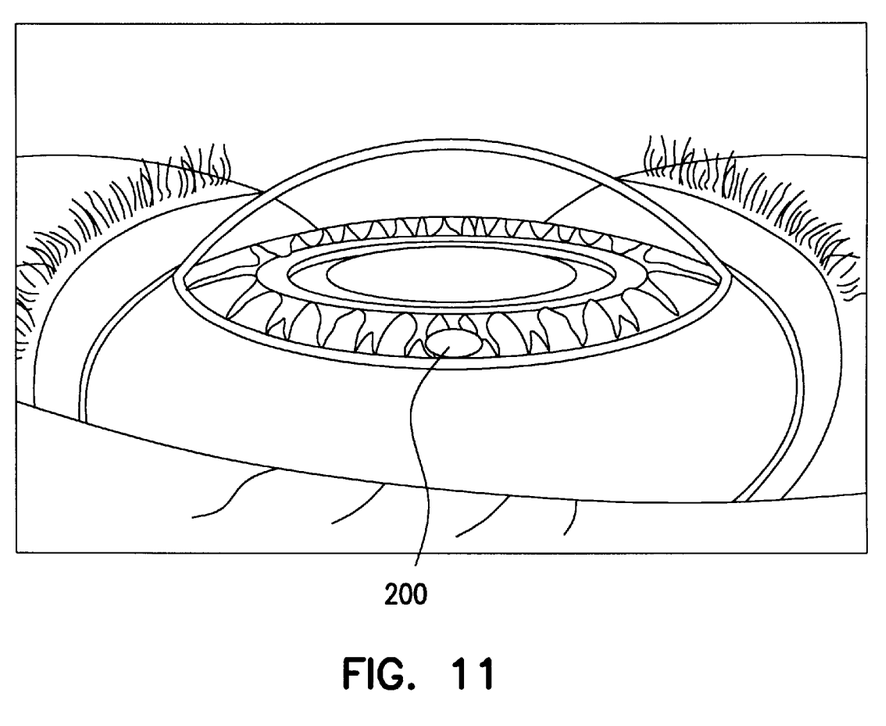
FIG. 11 is a partial outside view of the eye with the intraocular pressure monitoring/measuring apparatus attached on the iris.

FIGS. 9–11 illustrate various exemplary locations for attachment of the PRT 200 to the iris 102. It is noted that the PRT 200 as shown is not to scale for better visualization. FIG. 9 shows that the PRT 200 is attached to the front of the periphery of the iris 102 at the six o'clock position of a left eye. FIG. 10 shows that the PRT 200 is attached, by crimping the clamping device 700, around a portion of the iris 102 at the twelve o'clock position, while another attachment of a second PRT 200 may be attached, by using the barb 600, to a portion of the iris 102 at the six o'clock position. It is noted that for better visualization, the PRT 200 is not drawn to scale or located peripherally on the iris 102. FIG. 11 shows that the PRT 200 is located on the periphery of the iris 102 at the three o'clock position in a right eye as seen from the bridge of a nose.

In the above illustration, the apparatus 200 is preferably the PRT. The PRT is a miniature device such that it can be implanted into the eye. The PRT is operated by irradiating it with laser light. The PRT resonates to this light in such a way that is indicative of the pressure of the environment in which it resides. The resonance of the reflected laser light is proportional to the ambient pressure surrounding the device, e.g. within the eye. Alternatively, non-visible wavelengths of light can be used to penetrate the tissue of the iris. Use of this alternative allows placement of the PRT behind the iris, e.g. proximate to an intraocular lens, or as a part of an intraocular lens implant.

The theory for the PRT device can be found in an article by Zook et al., entitled "Optically Excited Self-Resonant Microbeams", published in Sensors and Acuators A 52 (1996), pages 92–98; or an article by Burns et al., entitled "Sealed-Cavity Resonant Microbeam Pressure Sensor", published in Sensors and Acuators A 48 (1995), pages 179–186. Briefly, highly modulated reflected light is produced by an interferometric structure composed of a microresonator and vacuum enclosure. This allows remote fiber-optic excitation and readout of the microbeam resonance frequency for single-point or multi-point sensing. The self-resonant configurations of a PRT device which use optics eliminate physical wiring to the outside and eliminate external circuitry required to maintain microbeam resonance. A PRT device is operated by irradiating the PRT device with a laser light. The PRT device resonates to the light in such a way that is indicative of the pressure of the environment in which it resides. The resonance of the reflected laser light is proportional to the ambient pressure surrounding the device, e.g. within the eye. Alternatively, if the PRT device is placed behind the iris, e.g. proximate to an intraocular lens, or as a part of an intraocular lens implant, non-visible wavelengths of light can be used. These frequencies of light will penetrate the tissue of the iris and interact with the device to monitor/measure the intraocular pressure. It will be appreciated that other types of suitable transducers and/or pressure sensors can be employed.

The apparatus 200 is a self-contained device. As discussed above, it can be fully encased in a material bio-compatible to the eye, such as silicone, acrylic, or polymethylmethacrylate (PMMA), and the like. Small holes can be made on the edges of the encasement to allow a suture to be strung thus attaching the apparatus 200 to the iris or other sites of the eye. Alternatively, a small clamp, preferably of the same material as the encasement, can be incorporated into the encasement. This allows the edge of the encasement to be clamped to the iris by simply crimping the clamp around some of the iris tissue. The attachment, such as suturing and clamping and using the prolene barb, is known in the art. It will be appreciated that other attachment embodiments can be used without departing from the principles of the present invention.

The apparatus 200 can be used as a stand-alone device by attaching the apparatus to the eye. It will be appreciated that the apparatus can also be used as a part of an intraocular lens implant as shown in FIGS. 3 and 4. In such a case, the apparatus and the intraocular lens can be arranged in a single unit.

The gauge pressure to be monitored/measured by the apparatus 200 preferably ranges from 0 to 80 mm Hg. Pressure accuracy is preferably within 1 mm Hg. Operating temperatures are optimally from 97° F. to 104° F. The laser is preferably a class II laser in red to near infrared wavelength.

In clinical applications, one advantage of the present invention is that it allows direct, accurate measurements of the intraocular pressure. Furthermore, pressures can be taken by shining a medically safe laser or other compatible non-visible light source onto the apparatus or the iris overlying the apparatus without having to touch the eye. This eliminates user variability in intraocular pressure measurements and allows patients to take pressure measurements at home. Further, no eye drops or puffs of air are necessary. Pressures may be measured with the eyelids closed, thus allowing 24-hour monitoring of intraocular pressures. Accordingly, the present invention allows development of diurnal intraocular pressure curves and thus making possible drug efficacy comparisons. It will be appreciated that there are many alternative uses of the present invention. For example, a PRT or other device similarly placed inside the eye could be used in conjunction with an external laser (or other light, electromagnetic, sonic, etc.) source for spectroscopic or similar analysis of the aqueous (fluid inside the front part of the eye). This may yield measurements of components of the aqueous such as levels of glucose, protein, electrolytes and the like. Since the aqueous of the eye is an ultrafiltrate of the blood and since levels of these components in the aqueous vary with levels of these components in the blood, such a device may be used for monitoring blood glucose levels in diabetic patients without the need for drawing blood, as an example. Levels of other components of the blood may similarly be implied, calculated or measured.

The preferred embodiment of the present invention has been described in detail. It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An apparatus capable of monitoring intraocular pressure in an eye having internal tissue comprising a polysilicon resonant transducer having an attachment to connect the transducer to the internal tissue of the eye.

2. The apparatus of claim 1, wherein the transducer is encased in a material which is bio-compatible with the eye.

3. The apparatus of claim 2, wherein the attachment includes an encasement with holes therethrough for suturing the apparatus to the internal tissue of the eye.

4. The apparatus of claim 2, wherein the attachment is a clamp for holding the transducer in the eye.

5. The apparatus of claim 2, wherein the attachment is a prolene barb for attaching the transducer to the iris.

6. The apparatus of claim 2, wherein the transducer is encased in a material made of silicone.

7. The apparatus of claim 2, wherein the transducer is encased in a material made of polymethylmethacrylate (PMMA).

8. The apparatus of claim 2, wherein the transducer is encased in a material made of an acrylic polymer.

9. The apparatus of claim 1, wherein the internal tissue is the iris on the anterior chamber side of the eye.

10. The apparatus of claim 1, wherein the internal tissue is the iris on the posterior chamber side of the eye.

11. The apparatus of claim 1, further comprising an intraocular lens, wherein the transducer is attached to the intraocular lens.

12. The apparatus of claim 1, wherein the transducer is small enough to allow implantation in the eye without impeding eye function.

13. The apparatus of claim 1, wherein the intraocular pressure is measured by irradiating the transducer with electromagnetic energy.

14. The apparatus of claim 13, wherein the electromagnetic energy is provided by a light source.

15. The apparatus of claim 14, wherein the light source is a laser.

16. An apparatus capable of monitoring intraocular pressure in an eye having internal tissue, comprising:

an energy source disposed external to the eye; and a polysilicon resonant transducer having an attachment to connect the transducer to the internal tissue of the eye, wherein upon activating the transducer by the energy source, the miniature pressure sensor monitors the intraocular pressure in the eye.

17. The apparatus of claim 16, wherein the energy source is a laser source.

18. The apparatus of claim 16, wherein the energy source is an electromagnetic source.

19. The apparatus of claim 16, further comprising an intraocular lens, wherein the transducer is attached to the intraocular lens.

20. A method of monitoring intraocular pressure in an eye having a polysilicon resonant transducer attached inside of the eye, comprising activating the transducer with an energy source to measure the pressure in the eye.

21. The method of claim 20, wherein the energy source is an electromagnetic energy source.

22. The method of claim 21, wherein the energy source is a light source.

23. The method of claim 22, wherein the light source is a laser.

24. The method of claim 20, wherein the transducer is attached with a clamp, a suture or a prolene barb.

* * * * *